US006437185B1

(12) United States Patent
Walele et al.

(10) Patent No.: US 6,437,185 B1
(45) Date of Patent: Aug. 20, 2002

(54) QUATERNARY AMMONIUM COMPOUNDS AND PROCESS FOR PREPARING AND USING SAME

(75) Inventors: Ismail I. Walele, Saddle Brook; Samad A. Syed, Paramus, both of NJ (US)

(73) Assignee: Finetex, Inc., Elmwood Park, NJ (US)

( * ) Notice: Subject to any disclaimer, the term of this patent is extended or adjusted under 35 U.S.C. 154(b) by 0 days.

(21) Appl. No.: 09/593,020

(22) Filed: Jun. 13, 2000

Related U.S. Application Data

(60) Provisional application No. 60/139,422, filed on Jun. 6, 1999.
(51) Int. Cl.[7] .................. C07C 213/00; C07C 215/02
(52) U.S. Cl. ......................... 564/293; 564/292
(58) Field of Search ................ 564/281, 291, 564/292, 293, 295, 296

(56) References Cited

U.S. PATENT DOCUMENTS

| | | |
|---|---|---|
| 2,654,785 A | 10/1953 | Miescher et al. |
| 2,668,854 A | 2/1954 | Miescher et al. |
| 4,126,562 A | 11/1978 | Goffinet et al. |
| 4,157,388 A | 6/1979 | Christiansen |
| 4,250,112 A | 2/1981 | Lobach et al. |
| 4,720,383 A | 1/1988 | Drach et al. |
| 4,764,306 A | 8/1988 | Login |
| 4,808,321 A | 2/1989 | Walliby |
| 4,913,828 A | 4/1990 | Caswell et al. |
| 4,997,912 A | 3/1991 | Wirtz et al. |
| 5,087,733 A | 2/1992 | Deppert et al. |
| 5,206,013 A | 4/1993 | Deppert et al. |
| 5,254,271 A | 10/1993 | Hamann et al. |
| 5,427,773 A | 6/1995 | Chaudhuri et al. |
| 5,427,774 A | 6/1995 | Chaudhuri et al. |
| 5,451,394 A | 9/1995 | Chaudhuri et al. |
| 5,863,526 A | 1/1999 | Yeung et al. |
| 5,916,863 A | 6/1999 | Iacubucci et al. |

*Primary Examiner*—Barbara P. Badio
(74) *Attorney, Agent, or Firm*—Weingram & Associates, P.C.

(57) ABSTRACT

Novel quaternary ammonium compounds are disclosed, as well as methods for their preparation and their use in the treatment of hair, fibers and textiles as softening and conditioning agents. The high substantivity of these novel quaternary ammonium compounds to hair, fibers, and textiles, and their mildness to the skin and eyes, make them well suited for softening and conditioning fibers for applications such as personal care, laundry, and textile use.

For example, quaternary ammonium compounds such as N',N'',N'''-Triethyl, N',N',N''', N'''-Tetramethyl, N''-[(Polyoxypropyi)-ω-hydroxyalkyl], dipropylene triammonium triethosulfate have been prepared. Quaternary ammonium compounds may also include those involving other reactive groups known to those skilled in the art.

22 Claims, No Drawings

QUATERNARY AMMONIUM COMPOUNDS AND PROCESS FOR PREPARING AND USING SAME

This application claims the benefit of U.S. Provisional Application No. 60/139,422 filed Jun. 16, 1999.

BACKGROUND OF THE INVENTION

1. Field of the Invention

The present invention relates to novel quaternary ammonium compounds, and more particularly to monomeric polyquaternary ammonium derivatives of substituted dipropylene triamine, their process of manufacture, their use in hair care products and in the treatment of fibers and textiles, and preparations containing the quaternary ammonium compounds.

The novel quaternary ammonium compounds of the invention have very high substantivity to fibers such as wool fiber, acrylic fibers, human hair and textiles made of wool and acrylic fibers or mixed fibers, with excellent conditioning and softening effects. By "mixed fibers" is meant a combination of polyester and cotton or rayon fibers, or polyester and wool fibers.

2. Description of the Related Art

Quaternary ammonium compounds are known for a variety of different applications.

U.S. Pat. Nos. 2,654,785 and 2,668,854 to Miescher discloses wholly or partially quaternated azalkane diamines. The quaternary ammonium compounds may be used as medication. The patent further discloses use of diethyl sulfate as a quaternating agent.

U.S. Pat. No. 4,126,562 to Goffinet et al. discloses non-ionic textile softening compositions comprising a cationic surfactant and a non-ionic fabric-conditioning substance selected from fatty acid esters of mono-or polyhydric alcohols having from 1 to 8 carbon atoms and anhydrides thereof. The composition may additionally comprise an insoluble cationic softener selected from di-C10-C22 alkyl quaternary ammonium salts and C8-C25 imidazolinium salts.

U.S. Pat. No. 4,250,112 to Lobach et al. discloses poly-alkylenepolyamines containing quaternary dialkylammonium groups and their use as agents for retention of fibers in the manufacture of papers.

U.S. Pat. No. 4,997,912 to Wirtz et al. discloses esters of oxalkylated alkylalkylenediamines, which may be quaternized, obtained by esterifying oxyalkylated alkylalkylenediamines. The compounds are used as corrosion inhibitors in crude oil recovery and treatment plants.

U.S. Pat. No. 4,157,388 to Christiansen discloses polycationic or polyquaternary ammonium ionenes, which generally are hygroscopic. The compounds are useful as conditioning agents for skin, hair and textile products.

U.S. Pat. No. 4,720,383 to Drach et al. discloses imidazolinium compounds used for softening and conditioning fibers, hair and skin. The patent discloses that it is known to prepare softeners comprising quaternaries of ethoxylated or nonethoxylated amido amines derived from the reaction of high molecular weight acid like stearic and a multi amine such as diethylenetriamine. The standard alkylating agents are diethyl sulfate or dimethyl sulfate.

U.S. Pat. No. 4,764,306 to Login discloses a process for the production of bis-quaternary ammonium compounds comprising contacting a tertiary amine with a neutralizing acid, such as HCL, and subsequently contacting the resulting mixture with an epoxide, preferably epihalohydrin or epichlorohydrin. The tertiary amine is preferably stearyl dimethyl amine or lauryl dimethyl amine. The resulting bis-quaternary ammonium compounds are incorporated into hair conditioners.

U.S. Pat. No. 4,808,321 to Walley discloses liquid fabric softening and antistatic compositions which contain monoester analogs of ditallow, dimethyl ammonium chloride.

U.S. Pat. No. 4,913,828 to Caswell et al. discloses alkyl amine-anionic surfactant ion-pair/wax composites useful as fiber, hair and fabric conditioning agents.

U.S. Pat. Nos. 5,087,733 and 5,206,013 to Deppert et al. disclose sulfur containing quaternary ammonium compounds, and their use as hair conditioning agents.

U.S. Pat. No. 5,254,271 to Hamann et al. discloses hair and fabric conditioning compositions comprising mixtures of quaternary ammonium compounds with or without ester groups prepared by reacting amines with dimerized fatty acids and subsequent quaternization or protonation with inorganic or organic acids.

U.S. Pat. Nos. 5,427,773; 5,427,774; and 5,451,394 to Chaudhuri et al. discloses non-irritating, hair, skin and textile substantive, quaternary ammonium salts of paradi-alkylamino benzamides. These benzamide derivatives are also active sunscreening agents.

U.S. Pat. No. 5,863,526 to Yeung et al. discloses a hair conditioning composition comprising homopolymers prepared from ammonium quaternary salts of amino alkylacrylamides.

U.S. Pat. No. 5,916,863 to Iacobucci et al. discloses a textile softening agent comprising a quaternary ammonium salt which comprises a mixture of mono-, di-, and tri-ester components, having high diester content and low triester content.

The references describe the production of cationic and quaternary ammonium compounds and their use in the treatment of hair, fiber and textiles as softening and conditioning agents. However, none of the references disclose or suggest the specific, novel quaternary ammonium compounds of the invention, a process of preparing same, or the use of such compounds in the treatment of fibrous materials.

Additionally, the substantivity characteristics of the quaternary ammonium compounds of the invention are superior to known quaternary ammonium compounds, and are stable in highly acidic or highly alkaline medium. These properties make the quaternary ammonium compounds of the invention suitable for use in specialized alkaline fiber or hair treatment systems such as in hair straightening treatments, at a high pH of 12.00, and also in permanent waving, at a pH of 9–10. The quaternary ammonium compounds of the invention are stable to these extreme pH conditions. The quaternary ammonium compounds of the invention also have very high substantivity to fibers such as wool fiber, acrylic fibers, human hair and textiles made of wool and acrylic fibers or mixed fibers, with excellent conditioning and softening effects, as shown in Examples 52 and 53 below.

OBJECTS AND SUMMARY OF THE INVENTION

It is an object of the present invention to provide a process for producing quaternary ammonium compounds which are very mild.

It is another object of the invention to provide a process for making quaternary ammonium compounds for use in the treatment of hair, fiber and textile materials.

It is yet another object of the invention to provide a process for making quaternary ammonium compounds for use in hair care products that allow the use and application of thio-based hair treatment specialties and formulations.

It is a further object of the invention to provide a process for making quaternary ammonium compounds which have very high substantivity to fibers such as wool fiber, acrylic fibers, human hair, and textiles made of wool and acrylic fibers or mixed fibers.

Yet another object of the invention is to provide a method for producing quaternary ammonium compounds for use in hair shampoo products which have excellent conditioning effects when used alone or in combination with other surfactants.

Another object of the invention is to provide a method of producing quaternary ammonium compounds which are stable in highly acidic or highly alkaline medium.

It is another object of the invention to provide quaternary ammonium compounds which are excellent conditioners and softeners for fibrous materials.

Yet another object of the invention is to provide quaternary ammonium compounds which are suitable for use in alkaline fiber or hair care systems such as hair straighteners and permanent wave treatments.

These and other objects are accomplished by providing a process for preparing quaternary ammonium compounds, and specifically monomeric, multi-charge, multi-functional quaternary ammonium compounds. These quaternary ammonium compounds are improved as compared to commercially available quaternary ammonium compounds, as they are milder and less irritating to the skin and eyes. Hair care formulations containing the quaternary ammonium compounds of the invention are conditioning and emollient, have very low toxicological profiles, and are not irritating to the skin and eyes.

DETAILED DESCRIPTION OF THE INVENTION

The novel guaternary ammonium compounds of this invention have unique properties in that they have very high substantivity to fibers such as wool fiber, acrylic fibers, human hair and textiles made of wool and acrylic fibers or mixed fibers. Such high substantivity is a useful property for allowing the application of these compounds to fibers, and especially- to human hair. The utility of such compounds in hair care products results in excellent conditioning and softening effects. The high substantivity of these novel quaternary ammonium compounds to hair, fibers, and textiles, and their mildness to the skin and eyes, make them well suited for softening and conditioning fibers for applications such as personal care, laundry, and textile use.

The novel quaternary ammonium compounds of the invention are preferably prepared by:

1. Reacting an Amine with alkoxide, preferably Propylene Oxide ("PO"), yielding a polyoxypropylene addict amine of alkoxide (hereinafter abbreviated "AMP"). The alkoxide is selected from the group consisting of propylene oxide, ethylene oxide, and a mixture of propylene oxide and ethylene oxide.

2. Reacting the adduct AMP of step 1 with a 1,2 epoxyalkane having from 3 to 28 carbon atoms (such as α-olefin epoxide, i.e., $C_{16}$-Epoxide) to produce the oxyalkylated condensate;

3. Further quaternizing the oxyalkylated condensate of step 2 with a suitable quaternization agent, preferably diethyl sulfate ("DES") or dimethyl sulfate ("DMS"), to produce a quaternary ammonium compound.

4. Optionally diluting the quaternary ammonium compound produced in Step 3 in water to obtain the desired concentration, preferably a 25% or 50% or 75% solids-liquid solution or dispersion.

The process of the invention provides a composition of matter comprising a monomeric polyquaternary ammonium derivative of an amine, preferably a substituted, dipropylene triamine. The preferred, highly substituted, dipropylene triamine which is used in the process of the invention is Tetramethyliminobis-Fropylamine, abbreviated herein as "AM". The propoxylation (or ethoxylation) step adds multiple units of oxypropyl or oxyethyl chains. This propoxylated adduct is then reacted with of $C_{16}$-α-olefin epoxide preferably one mole) to produce the oxyalkylated condensate, i.e., hydroxycetoxy-polyoxypropylated tetramethyliminobis propylamine. This hydroxycetoxy-polyoxypropylated tetramethyliminobis propylamine is then further quaternized with 3 moles of Diethyl Sulfate to yield a quaternary of this invention. The preferred molar ratio is 1:2 to 1:3 for full quaternization. The preferred molar ratio is 1.3.

The very mild quaternary ammonium compounds of the invention are particularly useful in fiber treatment, especially in hair treatment compositions that permit the application of thio-based hair treatments, and are suitable for use in alkaline fiber or hair care systems such as hair straighteners and permanent wave treatments. The quaternary ammonium compounds of the invention may be used in shampoos, conditioners., and conditioning shampoos. When the quaternary ammonium compounds of the invention are deposited on human hair, they improve the ability of the hair to be combed and provide an antistatic effect. This makes the hair more manageable.

The compounds of the present invention are generally semi-liquids at room temperatures. They mix and dissolve and disperse readily with most types of shampoo/conditioner formulations.

The quaternary ammonium compounds of the invention are excellent hair-conditioning agents, as stated above. They are also general antistats and humectants for fibrous textile products such as rayon and fiber glass, and anti-static agents for textile and rug products in general. The compounds of the invention are also effective as wash cycle conditioners and rewetting agents in some laundry detergent formulations. Thus, the quaternary ammonium compounds of the invention find application in compositions such as fabric detergent, shampoos, hair conditioners, and dryer- and washer-added fabric conditioners.

The foregoing list is only exemplary of the type of compositions in which the novel quaternary ammonium compounds of this invention may be used, and, as such, is not to be considered limiting.

The preferred, highly substituted, dipropylene triamine which is used in the process of the invention is Tetramethyliminobis-Propylanine, abbreviated herein as "AM", whose structure is:

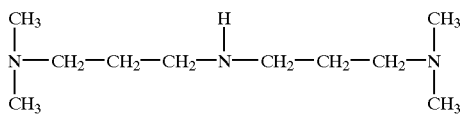

The propoxylation (or ethoxylation) step adds multiple units of oxypropyl (or oxyethyl chains) and produces a compound having the chemical name Poly(oxypropyl) Tetramethylimnobis propylamnine, which has the following structure:

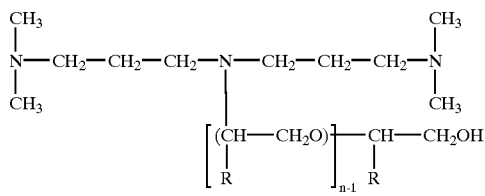

where

R=H (ethoxylated derivative);

R=CH$_3$ (propoxylated derivative); and n=1 to 100 moles of Ethylene Oxide ("EO") and/or Propylene Oxide ("PO").

Specifically, it is preferred to form a 3 mole Propoxylate of AM, abbreviated herein as AMP-3, having the chemical name Tri(oxypropyl) Tetramethyliminobis propylanine, and having the following structure:

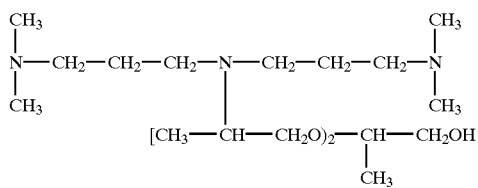

Alternatively, it is preferred to form a 5 mole Propoxylate of AM, abbreviated herein as AMP-5, having the chemical name Pentaoxypropyl-Tetrarnethyliminobis propylamine, which has the following structure:

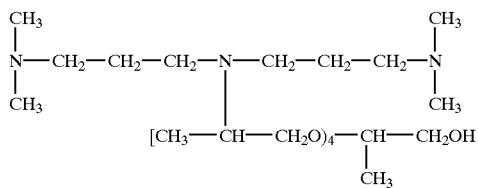

This propoxylated adduct is then reacted with a 1,2 epoxyalkane having from 3 to 28 carbon atoms, preferably with one mole of C$_{16}$-α-olefin epoxide (abbreviated herein as "C$_{16}$-Epoxide"), also known as 1,2-epoxycetane, or 1,2-epoxyhexadecane, which has the following structure:

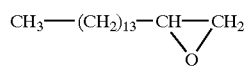

to produce an oxyalkylated condensate, namely, a hydroxycetylalkylated condensate of propxylate or ethoxylated tetrarnethyliminobis propylamine, which has the following structure:

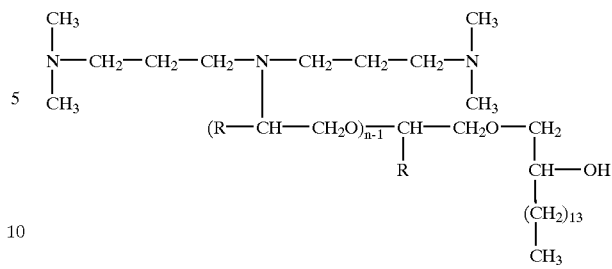

where

R=H (ethoxylated derivative);

R=CH$_3$ (propxylated derivative); and n=1 to 100 moles of EO and/or PO.

Specifically, AMP-3 is reacted with C$_{16}$-Epoxide to produce Tri(oxypropyl)-ω-hydroxycetyl-Tetramethyliminobis Propylamine, abbreviated herein as AMP-3-CT. AMP-5 is reacted with C$_{16}$-Epoxide to produce Pentaoxypropyl-ω-hydroxycetyl-Tetramethyliminobis Propylamine.

Alternatively, AMP-3 may be reacted with 1,2-Epcxydodecane/1,2-Epoxytetradecane to produce Tri(oxypropyl)-ω-hydroxy (lauryl/myristyl)= Tetramethyliminobis propylamine, abbreviated herein as AMP-3-LM, which has the following structure:

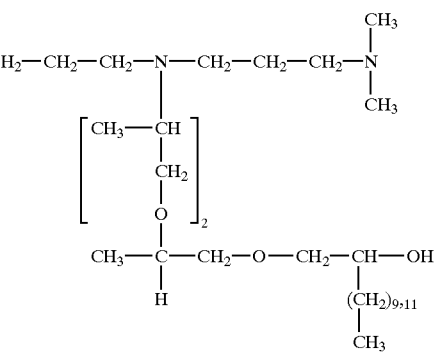

The hydroxyalkoxy-polyalkoxylated tetramethyliminobis propylamine is then quaternized with a quaternizing agent, preferably 3 moles of Diethyl Sulfate having the formula (C$_2$H$_5$)$_2$SO$_4$, to yield a quaternary ammonium compound of this invention, having the following generic structure:

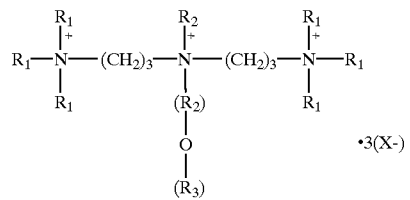

where R$_1$ = CH$_3$ and /or C$_2$H$_5$

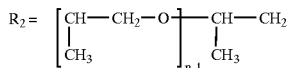

X= C$_2$H$_5$SO$_4$ or CH$_3$SO$_4$.

Specifically, the hydroxycetoxy-tri(oxypropylated) tetramethyliminobis propylamine is quaternized with Diethyl Sulfate having the formula $(C_2H_5)_2SO_4$, to yield a quaternary ammonium compound of this invention, having the following structure:

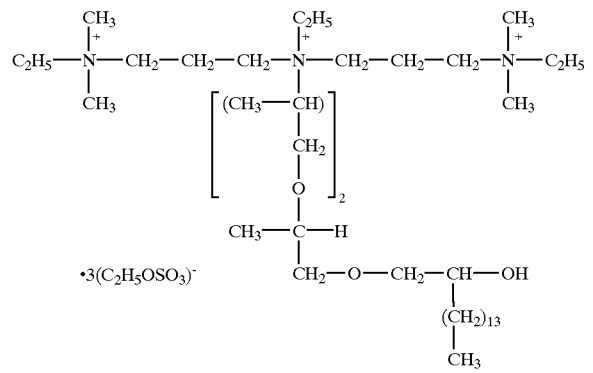

This quaternary ammonium compound has the trade name FINQUAT® CT-P (INCI Name: Quaternium 89), and the chemical name: N',N",N'"-Triethyl, N',N',N'",N'"-Tetramethyl, N"-[(Trioxypropyl)-ω-hydroxycetyl], dipropylene triammonium triethosulfate.

Quaternating agents such as alkyl or alkenyl halides, such as methyl chloride, methyl bromide or methyl iodide, or other dialkyl sulfates such as di-methyl sulfate may be used. The molar ratio of the oxyalkylated condensate to the quaternating agent is in the range of 1:2 to 1:3, with a 1:3 ratio being preferred.

This invention is also directed to the use of the quaternary ammonium compound produced by the method of the invention in treating hair, fiber, and textile materials. The quaternary compounds of the invention are particularly useful in fiber treatment, especially in hair treatment compositions that permit the application of thio-based hair treatments.

More particularly, the compounds of the invention may be obtained by the following method:
A. starting with 1 mole of tetramethyliminobis propylamine.
B. Adding to the compound of Step A from 1 to 100 moles of alkoxide, preferably either ethylene oxide or propylene oxide, or a mixture of ethylene oxide and propylene oxide, in any ratio.
C. Reacting each mole of the compound produced in Step B with from 0.90 to 1.0 mole of a 1,2 epoxyalkane having from 3 to 28 carbon atoms, preferably C16-α-olefin-Epoxide.
D. Quaternizing each mole of the compound produced in Step C with 2.5 to 3.00 moles of a suitable quaternization agent, such as diethyl sulfate or dimethyl sulfate.
E. Optionally diluting the quaternary compound produced in Step D in water to obtain the desired concentration, preferably a 25%–75% solids-liquid solution or dispersion, and most preferably a 70% concentration.

The quaternary ammonium compounds of the invention are poly-functional with 3 quaternary positions per mole of the molecule. This high density of quaternized nitrogens on the molecule allows the molecule to reach and attach to the anionic hair or fibers. Such an attachment offers antistatic effects besides being beneficial as conditioners and softeners. Furthermore, the feel imparted to hair and fibers/textiles is soft and oil free which is also an advantageous quality of the quaternary ammonium compounds of the invention.

The quaternary ammonium compounds of this invention may be used in treatment of hair, textiles and fabrics. The amount used in such applications is dependent on the type of compositions, the type and quantity of other ingredients used, and the amount and type of functional additives that are utilized.

Further, the quaternary ammonium compounds of this invention possess other unusual physio-chemical properties, which can make them beneficial and unique components of sophisticated treatment systems. Thus, the quaternary ammonium compounds described herein may serve not only as hair, textile and fiber treatment agents, but may also exhibit one or more other functions, such as adsorption on anionically charged particulate matter as in clays, pigments, etc.

The quaternary ammonium compounds have shown usefulness similar to conventional quaternary ammonium compounds with the additional benefits of being mild to the skin. Also, skin feel is even better than using conventional quaternary ammonium compounds.

In a specific embodiment, and by way of illustration, this invention contemplates the production of the following quaternary ammonium compounds:

1. Quaternary P3CT, Trade Name: FINQUAT CT-P (INCI Name: Quaternium 89) whose structure is set forth above and whose chemical name is N',N",N'"-Triethyl, N',N',N'", N'"-Tetramethyl, N"-[(Trioxypropyl)-ω-hydroxycetyl], dipropylene triammonium triethosulfate.

2. Quaternary P5CT, chemical name: N',N",N'"-Triethyl, N',N',N'",N'"-Tetramethyl, N"-[(Pentaoxypropyl-ω-hydroxycetyl], dipropylene triammonium triethosulfate, and whose structure is:

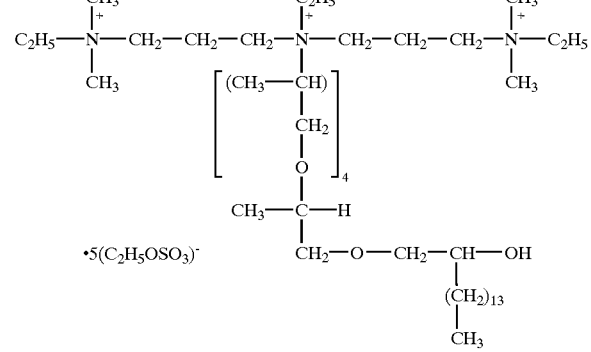

3. Quaternary P3LM, chemical name: N,N,N-Triethyl, N',N',N'",N'"-Tetramethyl, N"-[(Trioxypropyl),-ω-hydroxylauryl/myristyl], dipropylene triammonium triethosulfate, whose structure is:

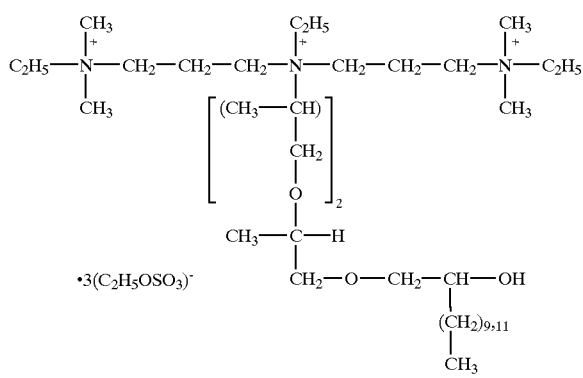

Some of these quaternary ammonium compounds are used in hair care formulations. Hair care formulations prepared according to the invention, which contain the quaternary ammonium compounds added thereto, can be formed, without limitation, into applications such as solutions, emulsions, gels, solids, emulsions, aerosols, powders, creams, granules, or tablets.

Mildness and emolliency of these quaternary ammonium compounds is of importance to the improved hair care products including the quaternary ammonium compounds of the invention. One major aspect of quaternary ammonium compounds of this invention is their very, very low to negligible toxicological effects indicating their mildness in hair care products.

Thus, the advantages of the quaternary ammonium compounds of the invention include:

Mildness of the formulations containing the quaternary ammonium compounds

Very low toxicological profile

Low irritation

Impart softer feel and better control of fibers

Thus, the novel quaternary ammonium compounds of this invention have unique properties in that they are mild to the skin, have very low to negligible toxicological effects, and very low eye and skin irritation. These properties make these quaternary ammonium compounds useful as vehicles or carriers, dispersants, emulsifiers, emollients, solubilizers and conditioners for hair care formulations such as hair creams, lotions, as well as other formulations. The foregoing list is only exemplary of the type of compositions in which the quaternary ammonium compounds of this invention may be used, and, as such, is not to be considered limiting.

The amount of such quaternary ammonium compounds to be used in such compositions is dependent on the type of hair care compositions, the desired dosage or amount of active ingredient to be delivered, the type and quantity of other ingredients, such as cosmetic ingredients used, the amount and type of functional additives that are utilized, the user's skin and hair type, and the severity and extent of the skin or hair condition, and other parameters that will be apparent to those skilled in the art. Generally, compositions containing the quaternary ammonium compounds of the invention are topically applied in effective amounts to the affected areas of the skin or to hair. Typically, the amount of quaternary ammonium compounds used ranges from about 0.5% to 10.0%, by weight, of the formulation.

The quaternary ammonium compounds of the invention have properties such as, being less greasy, less oily, low toxicity, ease of emulsification, acid and alkaline stability, the ability to form gels with suspending agents, water solubility/dispersibility, and the ability to be combined with many common hair care ingredients.

The following are non-limiting examples of processes for preparing the quaternary ammonium compounds compositions of the invention (Examples 1 to 51), comparative substantivity properties (Example 52), comparative conditioning properties (Example 53), and toxicology studies (Example 54). In the Examples, as well as throughout this application, the chemical and scientific symbols have their customary meanings and all percents are weight percents unless otherwise specified.

Example Nos. 1 through 51 identify quaternary ammonium compounds produced by the process of the invention. For ease of identification, each preparation is identified by both an Example Number and a Reference No., where applicable.

Although the Examples use only selected compounds and formulations, it should be understood that the examples are illustrative and not limited. Thus, any of the aforementioned Reactants A and B may be substituted according to the teachings of this invention in the following Examples.

TABLE I

| Abbreviations for Examples | |
|---|---|
| AM = | Tetramethyliminobis Propylamine |
| E = | Ethylene Oxide |
| P = | Propylene Oxide |
| AME3 = | 3 moles Ethoxylate of AM |
| AME5 = | 5 moles Ethoxylate of AM |
| AMP-3 = | 3 moles Propoxylate of AM |
| AMP-5 = | 5 moles Propoxylate of AM |
| AMP3-CT = | C16 Epoxide condensate of AMP3 |
| AMP5-CT = | C16 Epoxide condensate of AMP5 |
| AMP3LM = | C12–14 Epoxide Condensate of AMP-3 |
| DES = | Diethyl Sulfate |
| Quat P3CT = | DES Quaternary of AMP3CT |
| Quat P5CT = | DES Quaternary of AMP5CT |
| Quat P3LM = | DES Quaternary of AMP3LM |

EXAMPLE #1

(Ref. No. 117-158-A)

Preparation of AMP-3 (3 mole Propoxylate of AM)

10 moles, i.e., 1890 gms. of AM were reacted under nitrogen with 30 moles, i.e., 1740 gms. propylene oxide in a stainless steel reactor of 5 liter capacity. The reaction was kept at 120° C.–130° C. and 50–60 psi. Reaction was held there until exotherm subsided. The mass was checked for amine value before propoxylation and after propoxylation. The amine value before propoxylation was 890 mg KOH/g and amine value after propoxylation was 460 mg KOH/g, which compared well with the theoretical value of 464 mg KOH/g. The reactor was then cooled and brought to atmospheric pressure. The yield was 3630 gms. of amber liquid.

EXAMPLE #2

(Ref. No. 117-158-B)

Preparation of AMP-5 (5 mole Propoxylate of AM)

7 moles, i.e., 1323 gms. of AM was reacted under nitrogen with 35 moles, i.e., 2030 gms. propylene oxide in a stainless it steel reactor of 5 liter size. The reaction temperature was kept at 120° C.–130° C. and 50–60 psi. Reaction was held there until exotherm subsided. The mass was checked for amine value before propoxylation and after propoxylation.

The amine value before propoxylation was 890 mg KOH/g and amine value after propoxylation was 355 mg KOH/g, which compared well with the theoretical value of 351 mg KOH/g. The reactor was then cooled and brought to atmospheric pressure. The yield was 3353 gms. of amber liquid.

EXAMPLE #3

(Ref. No. 117-158-C)

Large Batch Preparation of AMP-3 (3 mole Propoxylate of AM)

5246 lbs. of AM was charged to an evacuated stainless steel reactor under nitrogen atmosphere. To this was added, in portions, 4839 lbs. of propylene oxide. Addition was done such that heat input and exotherm brought the temperature to 120° C.–130° C. and pressure of 50–60 psi. Reaction was held there until exotherm subsided and addition of propylene oxide was comnpleted. The reaction mass was checked after propoxylation for amine value, which came to 460 mg KOH/g. The amine value before propoxylation was 890 mg KOH/g. The amine value of 460 mg KOH/g compared well with the theoretical value of 464 mg KOH/g. The reactor was then cooled and brought to atmospheric pressure. The yield in the reactor was 10,085 lbs.

EXAMPLE #4

(118-298)

Preparation of AMP3CT (C16 Epoxide Condensate of AMP3)

In 1 liter four neck reaction flask with stirrer, condenser, and thermometer was charged 309.7 grams of Example #1, i.e. AMP3. Nitrogen flow was maintained throughout. To this was added 190.3 grams of C16-α-Olefin Epoxide. The initial alkalinity of this mixture was 281 mg KOH/g. The temperature was raised to 150 C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 497 grams.

EXAMPLE #5

(118-302)

Preparation of Quat P3CT (DES Quat of AMP3CT)

In a one liter four neck glass reaction flask was added 287.5 grams of AMP-3CT from Example #4 (reference 118-298). The inert atmosphere of nitrogen was maintained throughout. Temperature was raised to 55° C. at which time the addition of DES (diethyl sulfate) was started so that the exotherm came to approximately 85° C.–104° C. Total quantity of DES was 212.5 grams of which the first portion was 47.23 grams. The balance of DES was added in units of 35.41 grams at temperature of 100° C.–104° C. Each portion was reacted for 30 minutes before the next portion of DES was added. Alkalinity and pH were checked on the in-process sample. Alkalinity was 22 mg KOH/g and pH of 25% water solution was 5.8. Additional guantity of 17 grams DES was added and reacted for 30 minutes. Alkalinity was none and pH 25% solution in water was <1.0. Reaction was cooled to 80° C. Added 71 grams of 1,3-butylene glycol and the mass was mixed for 1 hour at 80° C. The mixture was then cooled to 30° C. The yield of 587 grams was obtained as semisolid paste. This is abbreviated as Quat P3CT.

EXAMPLE #6

(118-304)

Preparation of Aqueous Quat P3CT

In a 500 ml glass reaction flask was added 75 grams of the product of example #5 (i.e. Anhydrous Quat-P3CT) and 225 grams of water. Mixture was subjected to mixing and pH adjustments with a 25% sodium hydroxide solution. The pH was brought to 5.9. Mixture was brought to 80° C. under nitrogen. It was then subjected to a reduced pressure of 15"–20" Hg. and held there for one hour. 32 grams of the distillate was collected. Added 32 grams of water to the reaction flask and equalized the pressure to 1 atmosphere. Cooled to 30° C. The yield of this mixture was 300 grams in the form of fluid dispersion.

EXAMPLE #7

(121-18)

Preparation of AMP3CT (C16 Epoxide Condensate of AMP3)

In 1 liter four neck reaction flask with stirrer, condenser, and thermometer was charged 309.7 grams of example #1 i.e. AMP3. Nitrogen flow was maintained throughout. To this was added 190.3 grams of C16-α-olefin Epoxide. The initial alkalinity of this mixture was 281 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 498 grams.

EXAMPLE #8

(121-21)

Preparation of Quat P3CT (DES Quat of AMP3CT)

In a 1 liter four neck glass reaction flask was added 287.5 grams of AMP-3CT from example #7 (reference 121-18). The inert atmosphere of nitrogen was maintained throughout Temperature was raised to 55° C. at which time the addition of DES (diethyl sulfate) was started so that the exotherm came to approximately 85° C.–104° C. Total quantity of DES was 212.5 grams of which the first portion was 47.23 grams. The balance of DES was added in units of 35.41 grams at temperature of 100° C.–104° C. Each portion was reacted for 30 minutes before the next portion of DES was added. Alkalinity and pH were checked on the in-process sample. Alkalinity was 22 mg KOH/g and pH of 25%. Water solution was 5.8. Additional quantity of 22 grams of DES was added and reacted for 30 minutes. Alkalinity was none and pH 25%. Solution in water was <1.0. Reaction was cooled to 80° C. and added 71 grams of 1,3-butylene glycol and the mass was mixed for 1 hour at 80° C. The mixture was then cooled to 30° C. The yield of 597 grams was obtained as a semisolid paste. This is abbreviated as Quat P3CT.

EXAMPLE #9

(121-24)

Preparation of Aqueous Quat P3CT

In a 500 ml glass reaction flask was added 75 grams of the product of example #8 (i.e. Anhydrous Quat P3CT) and 225 grams of water. Mixture was subjected to mixing and pH adjustment with a 25% w/w sodium hydroxide solution. The pH was brought to 5.9. Mixture was brought to 80° C. under nitrogen. It was then subjected to a reduced pressure of 15"–20" Hg. and held there for 1 hour. 60 grams of the distillate was collected. Added 60 grams of water to the reaction flask and equalized the pressure to 1 atmosphere. Cooled to 30° C. The yield of this mixture was 300 grams in the form of a fluid dispersion.

EXAMPLE #10

(121-41A)

Preparation of Quat P3CT (DES Quat of AMP3CT)

In a 500 ml four neck glass reaction flask was added 172.5 grams of AMP3CT from example #7 (reference 121-18). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 34.77 grams. The balance of DES was added in units of 11.60 grams at temperature of 100° C.–104° C. Each portion was reacted for 30 minutes before the next portion of DES was added. Alkalinity and pH was checked on the in-process sample. Alkalinity was 20 mg KOH/g and pH of 25% water solution was 5.95. Reaction was cooled to 80° C. The yield of 300 grams was obtained as solid paste. This is abbreviated as Quat P3CT.

EXAMPLE #11

(121-44)

Preparation of Aqueous Quat P3CT

In a 500 ml glass reaction flask was added 75 grams of the product of example #10 (121-41A) (i.e.Anhydrous Quat P3CT) and 225 grams of water. Mixture was subjected to mixing and without pH adjustment. Mixture was brought to 80° C. under nitrogen. It was then subjected to a reduced pressure of 15"–20" Hg. Hg and held there for 1 hour. 22 grams of the distillate were collected. Added 22 gms. of the water to the reaction flask and equalized the pressure to 1 atmosphere. Cooled to 30° C. The yield of this mixture was 300 gms. in the form of a fluid dispersion.

EXAMPLE #12

(121-25)

Preparation of AMP3CT (C16 Epoxide Condensate of AMP3)

In 1 litre four neck reaction flask with stirrer, condenser, and thermometer was charged 309.7 grams of example #1 i.e. AMP3. Nitrogen flow was maintained throughout. To this was added 190.3 grams of C16-α-Olefin Epoxide. The initial alkalinity of this mixture was 283 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. The yield was 498 grams.

EXAMPLE #13

(121-26)

Preparation of Quat P3CT (DES Quat of AMP3CT)

In a 1 litre four neck glass reaction flask was added 287.5 grams of AMP-3CT from example #12 (reference 121-25). The inert atmosphere of nitrogen was maintained throughout. Temperature was raised to 55° C. at which time the addition of DES (diethyl sulfate) was started so that the exotherm came to approximately 85° C.–104° C. Total quantity of DES was 212.5 grams of which the first portion was 47.23 grams. The balance of DES was added in units of 34.71 grams at temperature of 100° C.–104° C. Each portion was reacted for 30 minutes before the next portion of DES was added. Alkalinity and pH was checked on the in-process sample. Alkalinity was 22 mg KOH/g and pH of 25% water solution was 5.8. Additional quantity of 32 grams of DES was added and reacted for 30 minutes. Alkalinity was none and pH 25% solution in water was <1.0. Reaction was cooled to 80° C. Added 71 grams of 1,3-butylene glycol and the mass was mixed for 1 hour at 80° C. The mixture was then cooled to 30° C. The yield of 609 grams was obtained as a semisolid paste. This is abbreviated as Quat P3CT.

EXAMPLE #14

(121-28)

Preparation of Aqueous Quat P3CT

In a 500 ml glass reaction flask was added 75 grams of the product of example #13 (i.e. anhydrous Quat P3CT) and 225 grams of water. Mixture was subjected to mixing and pH adjustments with a 25% w/w sodium hydroxide solution. The pH was brought to 5.9. Mixture was brought to 80° C. under nitrogen. It was then subjected to a reduced pressure of 15"–20" Hg. and held there for 1 hour. 32 grams of distillate were collected. Added 32 grams of water to the reaction flask and equalized the pressure to 1 atmosphere. Cooled to 30° C. The yield of this mixture was 300 grams in the form of a fluid dispersion.

EXAMPLE #15

(121-31)

Preparation of Quat P3CT (DES Quat of AMP3CT)

In a 500 ml four neck glass reaction flask was added 172.5 grams of AMP-3CT from example #12 (reference 121–25). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in units of 17.92 grams at temperature of 100° C.–104° C. Each portion was reacted for 30 minutes before the next portion of DES was added. Alkalinity and pH was checked on the in-process sample. Alkalinity was 22 mg KOH/g and pH of 25% water solution was 5.8. Additional quantity of 10 grams DES was added and reacted for 30 minutes. Alkalinity was none and pH 25% solution in water was <1.0. Reaction was cooled to 80° C. Added 42 grams of 1,3-butylene glycol and the mass was mixed for 1 hour at 80° C. The mixture was then cooled to 30° C. The yield of 350 grams was obtained was a semisolid paste. This is abbreviated as Quat P3CT.

EXAMPLE #16

(121-32)

Preparation of Aqueous Quat P3CT

In a 500 ml glass reaction flask was added 75 gms. of the product of example #15 (i.e. anhydrous Quat P3CT) and 225 gms. of water. Mixture was subjected to mixing and pH adjustments with a 25% w/w sodium hydroxide solution. The pH was brought to 5.9. Mixture was brought to 80° C. under nitrogen. It was then subjected to a reduced pressure of 15"–20" Hg. and held there for 1 hour. 21 grams of the distillate was collected. Added 21 grams of water to the reaction flask and equalized the pressure to 1 atmosphere. Cooled to 30° C. The yield of this mixture was 300 grams in the form of a fluid dispersion.

EXAMPLE #17

(121-38)

Preparation of Quat P3CT (DES Quat of AMP3CT)

In a 500 ml four neck glass reaction flask was added 172.5 grams of AMP-3CT from example #4 (reference 118-298). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in units of 17.92 grams at temperature of 100° C.–104° C. Each portion was reacted for 30 minutes before the next portion of DES was added. Alkalinity and pH were checked on the in-process sample. Alkalinity was 22 mg KOH/g and pH of 25% water solution was 5.8. Additional quantity of 7.5 grams DES was added and reacted for 30 minutes. Alkalinity was none and pH 25% solution in water was <1.0. Reaction was cooled to 80° C. Added 42.6 grams of 1,3-butylene glycol and the mass was mixed for 1 hour at 80° C. The mixture was then cooled to 30° C. The yield of 351 grams was obtained as a semi-fluid paste. This is abbreviated as Quat P3CT.

EXAMPLE #18

(121-40)

Preparation of Aqueous Quat P3CT

In a 500 ml glass reaction flask was added 75 gms. of the product of example #17 (i.e. anhydrous Quat P3CT) and 225 gms. of water. Mixture was subjected to mixing and pH adjustments with a 25% w/w sodium hydroxide solution. The pH was brought to 5.9. Mixture was brought to 80° C. under nitrogen. It was then subjected to a reduced pressure of 15"–20" Hg. and held there for 1 hour. 26 grams of the distillate was collected. Added 26 grams of water to the reaction flask and equalized the pressure to 1 atmosphere. Cooled to 30° C. The yield of this mixture was 300 grams in the form of a fluid dispersion.

EXAMPLE #19

(121-41)

Preparation of Quat P3CT (DES Quat of AMP3CT)

In a 500 ml four neck glass reaction flask was added 172.5 grams of AMP-3CT from example #7 (reference 121-18). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in units of 17.92 grams at temperature of 100° C.–104° C. Each portion was reacted for 30 minutes before the next portion of DES was added. Alkalinity and pH was checked on the in-process samples. Alkalinity was 22 mg KOH/g and pH of 25% water solution was 5.8. Reaction was cooled to 80° C. Added 42 grams of 1,3-butylene glycol and the mass was mixed for 1 hour at 800C. The mixture was then cooled to 30° C. The yield of 342 grams was obtained as a semi-fluid paste. This is abbreviated as Quat P3CT.

EXAMPLE #20

(121-45)

Preparation of Aqueous Quat P3CT

In a 500 ml glass reaction flask was added 75 gms. of the product of example #19 (i.e. anhydrous Quat P3CT) and 225 gms. of water. Mixture was brought to 80° C. under nitrogen. It was then subjected to a reduced pressure of 15"–20" Hg and held there for 1 hour. 24 grams of the distillate was collected. Added 24 grams of water to the reaction flask and equalized the pressure to 1 atmosphere. Cooled to 30° C. The yield of this mixture was 300 grams in the form of a fluid dispersion.

EXAMPLE #21

(121-46)

Preparation of AMP3CT (C16 Epoxide Condensate of AMP3)

In 1 liter four neck reaction flask with stirrer, condenser, and thermometer was charged 309.7 grams example #1, i.e., AMP3. Nitrogen flow was maintained throughout. To this was added 190.3 grams of C16-α-Olefin Epoxide. The initial alkalinity of this mixture was 286 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 498 grams.

EXAMPLE #22

(121-47A)

Preparation of Quat P3CT (DES Quat of AMP3CT)

In a 1 liter four neck glass reaction flask was added 287.5 grams of AMP-3CT from example #21 (reference 121-46). The inert atmosphere of nitrogen was maintained throughout. Temperature was raised to 55° C. at which time the addition of DES (diethyl sulfate) was started so that the exotherm came to approximately 85° C.–104° C. Total quantity of DES was 170.0 grams of which the first portion was 36 grams. The balance of DES was added in units of 24 grams at temperature of 100° C.–104° C. Each portion was reacted for 30 minutes before the next portion of DES was added. Alkalinity and pH was checked on the in-process sample. Alkalinity was 20 mg KOH/g and pH of 25% water solution was 5.95. Reaction was cooled to 80° C. The yield of 480 grams was obtained as a solid paste.

This is abbreviated as Quat P3CT.

EXAMPLE #23

(121-49)

Preparation of Aqueous Quat P3CT

In a 500 ml glass reaction flask was added 75 grams of the product of example #22 (i.e. anhydrous Quat P3CT) and 225 gms. of water. Mixture was brought to 80° C. under nitrogen. It was then subjected to a reduced pressure of 15"–20" Hg and held there for 1 hour. 31 grams of the distillate was collected. Added 31 grams of water to the reaction flask and equalized the pressure to 1 atmosphere. Cooled to 30° C. The yield of this mixture was 300 grams in the form of a fluid dispersion.

EXAMPLE #24

(121-47)

Preparation of Quat P3CT (DES Quat of AMP3CT)

In a 1 liter four neck glass reaction flask was added 287.5 grams of AMP-3CT from example #21 (reference 121-46). The inert atmosphere of nitrogen was maintained throughout. Temperature was raised to 55° C. at which time the addition of DES (diethyl sulfate) was started so that the exotherm came to approximately 85° C.–104° C. Total quantity of DES was 170.0 grams of which the first portion was 36 grams. The balance of DES was added in units of 24 grams at temperature of 100° C.–104° C. Each portion was reacted for 30 minutes before the next portion of DES was added. Alkalinity and pH were checked on the in-process sample. Alkalinity was 22 mg KOH/g and pH 25% solution in water was 5.8. Reaction was cooled to 80° C. Add 72 grams of 1,3 butylene glycol and the mass was mixed for 1 hour at 80° C. The mixture was then cooled to 30° C. The yield of 550 grams was obtained as a semi-solid paste. This is abbreviated as Quat P3CT.

EXAMPLE #25

(121-50)

Preparation of Aqueous Quat P3CT

In a 500 ml glass reaction flask was added 75 grams of the product of example #24 (i.e. anhydrous Quat P3CT) and 225 gms. of water. Mixture was brought to 80° C. under nitrogen. It was then subjected to a reduced pressure of 15"–20" Hg and held there for 1 hour. 31 grams of the distillate was collected. Added 31 grams of water to the reaction flask and equalized the pressure to 1 atmosphere. Cooled to 30° C. The yield of this mixture was 300 grams in the form of a fluid dispersion.

EXAMPLE #26

(121-151A)

Preparation of Quat P3CT (DES Quat of AMP3CT)

In a 500 ml four neck glass reaction flask was added 172.5 grams of AMP-3CT from example #21 (reference 121-46). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in units of 17.92 grams at temperature of 100° C.–104° C. Each portion was reacted for 30 minutes before the next portion of DES was added. Alkalinity and pH were checked on the in-process sample. Alkalinity was 22 mg KOH/g and pH of 25% water solution was 5.8. Additional quantity of 7 grams DES was added and reacted for 30 minutes. Alkalinity was none and pH 25% solution in water <1.0. Reaction was cooled to 80° C. The yield of 305 grams was obtained as a solid paste. This is abbreviated as Quat P3CT.

EXAMPLE #27

(121-53)

Preparation of Aqueous Quat P3CT

In a 500 ml glass reaction flask was added 75 grams of the product of example #26 (i.e. anhydrous Quat P3CT) and 225 gms. of water. Mixture was subjected to mixing and pH adjustment with a 25% w/w sodium hydroxide solution. The pH was brought to 5.9. Mixture was brought to 80° C. under nitrogen. It was then subjected to a reduced pressure of 15"–20" Hg and held there for 1 hour. Added 26 grams of water to the reaction flask and equalized the pressure to 1 atmosphere. Cooled to 30° C. The yield of this mixture was 300 grams in the form of a fluid dispersion.

EXAMPLE #28

(121-51)

Preparation of Quat P3CT (DES Quat of AMP3CT)

In a 500 ml four neck glass reaction flask was added 172.5 grams of AMP-3CT from example #21 (reference #121-46). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in units of 17.92 grams at temperature of 100° C.–104° C. Each portion was reacted for 30 minutes before the next portion of DES was added. Alkalinity and pH were checked on the in-process sample. Alkalinity was 22 mg KOH/g and pH of 25% water solution was 5.8. Additional quantity of 7 grams DES was added and reacted for 30 minutes. Alkalinity was none and pH 25% solution in water was <1.0. Reaction was cooled to 80° C. Added 42 grams of 1,3-butylene glycol and the mass was mixed for 1 hour at 80° C. The mixture was then cooled to 30° C. The yield of 345 grams was obtained as a semisolid paste. This is abbreviated as Quat P3CT.

EXAMPLE #29

(121-54)

Preparation of Aqueous Quat P3CT

In a 500 ml glass reaction flask was added 75 grams of the product of example #28 (i.e. anhydrous Quat of P3CT) and 225 gms. of water. Mixture was subjected to mixing and pH adjustment with a 25% w/w sodium hydroxide solution. The pH was brought to 5.9. Mixture was brought to 80° C. under nitrogen. It was then subjected to a reduced pressure of 15"–20" Hg and held there for 1 hour. 22 grams of the distillate was collected. Added 22 grams of water to the reaction flask and equalized the pressure to 1 atmosphere. Cooled to 30° C. The yield of this mixture was 300 grams in the form of a fluid dispersion.

EXAMPLE #30

(121-57)

Preparation of AMP3CT (C16 Epoxide Condensate of AMP3)

In 500 ml. four neck reaction flask with stirrer, condenser, and thermometer was charged 185.82 grams example #1, i.e., AMP3. Nitrogen flow was maintained throughout. To this was added 114.18 grams of C16-α-Olefin Epoxide. The initial alkalinity of this mixture was 282 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 300 grams.

EXAMPLE #31

(121-60A)

Preparation of Quat P3CT (DES Quat of AMP3CT)

In a 500 ml four neck glass reaction flask was added 172.5 grams of AMP3CT from example #30 (reference 121-57). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in units of 17.92 grams at temperature of 100° C.–104° C. Each portion was reacted for 30 minutes before the next portion of DES was added. Alkalinity and pH were checked on the in-process sample. Alkalinity was 20 mg KOH/g and pH of 25% water solution was 5.95. Reaction was cooled to 80° C. The yield of 300 grams was obtained as solid paste. This is abbreviated as Quat P3CT.

EXAMPLE #32

(121-62)

Preparation of Aqueous Quat P3CT

In a 500 ml glass reaction flask was added 75 grams of the product of example #31 (i.e. anhydrous Quat P3CT) and 225 grams of water. Mixture was brought to 80° C. under nitrogen. It was then subjected to a reduced pressure of 15"–20" Hg and held there for 1 hour. 18 grams of the distillate were collected. Added 18 grams of water to the reaction flask and equalized the pressure to 1 atmosphere. Cooled to 30° C. The yield of this mixture was 300 grams in the form of a fluid dispersion.

EXAMPLE #33

(121-60B)

Preparation of Quat P3CT (DES Quat of AMP3CT)

In a 500 ml four neck glass reaction flask was added 172.5 grams of AMP3CT from example #30 (reference 121-57). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in the units of 17.92 grams at temperature of 100° C.–104° C. Each portion was reacted for 30 minutes before the next portion of DES was added. Alkalinity and pH were checked on the in-process sample. Alkalinity was 22 mg KOH/g and pH of 25% water solution was 5.8. Reaction was cooled to 80° C. Added 42.6 grams of 1,3-butylene glycol and the mass was mixed for 1 hour at 80° C. The mixture was then cooled to 30° C. The yield of 340 grams was obtained as a semi-fluid paste. This is abbreviated as Quat P3CT.

EXAMPLE #34

(121-63)

Preparation of Aqueous Quat P3CT

In a 500 ml glass reaction flask was added 75 grams of the product of example #33 (i.e. anhydrous Quat P3CT) and 225 grams of water. Mixture was brought to 80° C. under nitrogen. It was then subjected to a reduced pressure of 15"–20" Hg and held there for 1 hour. 20 grams of the distillate were collected. Added 20 grams of water to the reaction flask and equalized the pressure to 1 atmosphere. Cooled to 30° C. The yield of this mixture was 300 grams in the form of a fluid dispersion.

EXAMPLE #35

(121-59)

Preparation of AMP3CT (C16 Epoxide Condensate of AMP3)

In 500 ml reaction flask with stirrer, condenser, and thermometer was charged 185.82 grams example #1 i.e., AMP3. Nitrogen flow was maintained throughout. To this was added 114.18 gms. of C16-α-Olefin Epoxide. The initial alkalinity of this mixture was 282 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 300 gms.

EXAMPLE #36

(121-64A)

Preparation of Quat P3CT (DES Quat of AMP3CT)

In 500 ml four neck glass reaction flask was added 172.5 grams of AMP-3CT from example #35 (reference 121-59). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 gms. of which the first portion was 22.4 grams. The balance of DES was added in units of 17.92 grams at temperature of 100° C.–104° C. Each portion was reacted for 30 minutes before the next portion of DES was added. Alkalinity and pH were checked on the in-process sample. Alkalinity was 22 mg KOH/g and pH of 25% water solution was 5.8. Additional quantity of 15 grams DES was added and reacted for 30 minutes. Alkalinity was none and pH 25% solution in water <1.0. Reaction was cooled to 80° C. The yield of 315 grams was obtained as a solid paste. This is abbreviated as Quat P3CT.

EXAMPLE #37

(121-66)

Preparation of Aqueous Quat P3CT

In 500 ml four neck reaction flask was added 75 gms. of the product of example #36 (i.e. anhydrous Quat P3CT) and 225 grams of water. Mixture was subjected to mixing and pH adjustments with a 25% sodium hydroxide solution. The pH was brought to 5.9. Mixture was brought to 80° C. under nitrogen. It was then subjected to a reduced pressure of 15"–20" Hg. and held there for 1 hour. 40 grams of distillate were collected. Added 40 grams of water to the reaction flask and equalized the pressure to 1 atmosphere. Cooled to 30° C. The yield of this mixture was 300 gms. in the form of a fluid dispersion.

EXAMPLE #38

(121-64)

Preparation of Quat P3CT (DES Quat of AMP3CT)

In a 500 ml four neck reaction flask was added 172.5 grams of AMP-3CT from example #35 (reference #121-59). The inert atmosphere of nitrogen was maintained throughout. Temperature was raised to 55° C. at which time the addition of DES (diethyl sulfate) was started so that the exotherm came to approximately 85° C.–104° C. Total quantity of DES was 127.5 grams of which the first portion was 22.4 grams. The balance of DES was added in units of 17.92 grams at temperature of 100° C.–104° C. Each portion was reacted for 30 minutes before the next portion of DES was added. Alkalinity and pH were checked on the in-process sample. Alkalinity was 22 mg KOH/g and pH of 25% water solution was 5.8. Additional quantity of 15 grams DES was added and reacted for 30 minutes. Alkalinity is none and pH 25% solution in water was <1.0. Reaction was cooled to 80° C. Added 42 grams of 1,3-butylene glycol and the mass was mixed for 1 hour at 80° C. The mixture was then cooled to 30° C. The yield of 355 grams was obtained as a semisolid paste. This is abbreviated as Quat P3CT.

EXAMPLE #39

(121-67)

Preparation of Aqueous Quat P3CT

In a 500 ml glass reaction flask was added 75 gms. of the product of example #38 (i.e. anhydrous Quat P3CT) and 225 grams of water. Mixture was subjected to mixing and pH adjustment with a 25% w/w sodium hydroxide solution. The pH was brought to 5.9. Mixture was brought to 80° C. under nitrogen. It was then subjected to a reduced pressure of 15"–20" Hg. and held there for 1 hour. 36 grams of distillate were collected. Added 36 grams of water to the reaction flask and equalized the pressure to 1 atmosphere. Cooled to 30° C. The yield of this mixture was 300 grams in the form of a fluid dispersion.

EXAMPLE #40

(118-299)

Preparation of AMP5CT (C16 Epoxide Condensate of AMP5)

In 1 liter four neck reaction flask with stirrer, condenser, and thermometer was charged 339 grams example #2, i.e., AMP5. Nitrogen flow was maintained throughout. To this was added 161 grams of C16-α-Olefin Epoxide. The initial alkalinity of this mixture was 239.89 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 499 grams.

EXAMPLE #41

(118-305)

Preparation of Quat P5CT (DES Quat of AMP5CT)

In a 1 liter four neck glass reaction flask was added 306.7 grams of AMP-5CT from example #40 (reference #118-299). The inert atmosphere of nitrogen was maintained throughout. Temperature was raised to 55° C. at which time the addition of DES (diethyl sulfate) was started so that the exotherm came to approximately 85° C.–104° C. Total quantity of DES was 193.3 grams of which the first portion was 36.24 grams. The balance of DES was added in units of 24.16 at temperature of 100° C.–104° C. Each portion was reacted for 30 minutes before the next portion of DES was added. Alkalinity and pH were checked on the in-process sample. Alkalinity was 18 mg KOH/g and pH of 25% water solution was 4.4. Additional quantity of 15 grams DES was added and reacted for 30 minutes. Alkalinity was none and pH 25% solution in water was <1.0. Reaction was cooled to 80° C. Added 70 grams of 1,3-butylene glycol and the mass was mixed for 1 hour at 80° C. The mixture was then cooled to 30° C. The yield of 585 grains was obtained as a semisolid paste. This is abbreviated as Quat P5CT.

EXAMPLE #42

(118-308)

Preparation of Aqueous Quat P5CT

In a 500 ml glass reaction flask was added 75 grams of the product of example #41 (i.e. anhydrous Quat P5CT) and 225 grams of water. Mixture was subjected to mixing and pH adjustments with a 25% w/w sodium hydroxide solution. The pH was brought to 5.7. Mixture was brought to 80° C. under nitrogen. It was then subjected to a reduced pressure of 15"–20" Hg and held there for 1 hour. 30 grams of distillate were collected. Added 30 grams of water to the reaction flask and equalized the pressure to 1 atmosphere. Cooled to 30° C. The yield of this mixture was 300 grams in the form of a fluid dispersion.

EXAMPLE #43

(117-75)

Preparation of AM23CT (C16 Epoxide Condensate of AMP3)

In 1 liter four neck reaction flask with stirrer, condenser, and thermometer was charged 434 grams example #1, i.e., AMP3. Nitrogen flow was maintained throughout. To this was added 266 grams of C16-α-Olefin Epoxide. The initial alkalinity of this mixture was 280.22 mg KOH/g. The temperature was raised to 150° C. with continued nitrogen atmosphere. Reaction was continued at 150° C. For the duration of 2 hours. The alkalinity remained constant ridicating that there was no loss of amine equivalence. The reaction mass was a dark amber liquid. Upon cooling to 30° C. the yield was 700 grams.

EXAMPLE #44

(117-79)

Preparation of Quat P3CT (DES Quat of AMP3CT)

In a 1 liter four neck glass reaction flask was added 402.50 grams of AMP-3CT from example #43 (reference 117-75). The inert atmosphere of nitrogen was maintained throughout Temperature was raised to 55° C. at which time the addition of DES (diethyl sulfate) was started so that the exotherm came to approximately 85° C.–104° C. Total quantity of DES was 297.50 grams of which the first portion was 75 grams. The balance of DES was added in units of 42 grams at temperature of 100° C.–104° C. Each portion was reacted for 30 minutes before the next portion of DES was added. Alkalinity and pH were checked on the in-process samples. Alkalinity was 6.23 mg KOH/g and pH of 25% water solution was 3.5. Reaction was cooled to 80° C. Added 100 grams 1,3-butylene glycol and the mass was mixed for 1 hour at 80° C. The mixture was then cooled to 30° C. The yield of 795 grams was obtained as a semisolid paste. This is abbreviated as Quat P3CT.

EXAMPLE #45

(118-292)

Preparation of Aqueous Quat P3CT

In a 500 ml glass reaction flask was added 75 grams of the product of example #44 (i.e. anhydrous Quat P3CT) and 225 grams of water. Mixture was subjected to mixing and pH adjustments with a 25% w/w sodium hydroxide solution. The pH was brought to 5.9. Mixture was brought to 80° C. under nitrogen. It was then subjected to a reduced pressure of 15"–20" Hg. and held there for 1 hour. 30 grams of the distillate were collected. Added 30 grams of water to the reaction flask and equalized the pressure to 1 atmosphere. Cooled to 30° C. The yield of this mixture was 30 grams in the form of a fluid dispersion.

EXAMPLE #46

(117-77)

Preparation of AMP5CT (C16 Epoxide Condensate of AMP5)

In 1 liter four neck reaction flask with stirrer, condenser, and thermometer was charged 474.60 grams of example #2, i.e., (AMP5. Nitrogen flow was maintained throughout. To this was added 225.40 grams of C16-α-Olefin Epoxide. The initial alkalinity was 230 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 700 grams.

EXAMPLE #47

(117-81)

Preparation of Quat PSCT (D-S Quat of AM?5CT)

In a 1 liter four neck glass reaction flask was added 429.38 grams of AMP-5CT from example #46 (reference 117-77). The inert atmosphere of nitrogen was maintained throughout. Temperature was raised to 55° C. at which time the addition of DES (diethyl sulfate) was started so that the exotherm came to approximately 85° C.–104° C. Total quantity of DES was 270.62 grams of which the first portion was 70 grams. The balance of DES was added in units of 30 grams at temperature of 100° C.–104° C. Each portion was reacted for 30 minutes before the next portion of DES was added. Alkalinity and pH were checked on the in-process sample, Alkalinity was 4.93 mg KOH/g and pH of 25% water solution was 3.8. Reaction was cooled to 80° C. Added 100 grams of 1,3-butylene glycol and the mass was mixed for 1 hour at 80° C. The mixture was then cooled to 30° C. The yield of 795 grams was obtained as a semisolid paste. This is abbreviated as Quat P3CT.

EXAMPLE #48

(118-293)

Preparation of Aqueous Quat P5CT

In a 500 ml glass reaction flask was added 75 grams of the product on example #47 (i.e. anhydrous Quat P5CT) and 225 grams of water. Mixture was subjected to mixing and pH adjustments with a 25% w/w sodium hydroxide solution. The pH was brought to 5.9. Mixture was brought to 80° C. under nitrogen. It was then subjected to a reduced pressure of 15"–20" Hg and held there for 1 hour. 36 grams of the distillate were collected. Added 36 grams of water to the reaction flask and equalized the pressure to 1 atmosphere. Cooled to 30° C. The yield of this mixture was 300 grams in the form of a fluid dispersion.

EXAMPLE #49

(121-95)

Preparation of AMP3LM (C12–C14 Epoxide Condensate of AMP3)

In 500 ml four neck reaction flask with stirrer, condenser, and thermometer was charged 167.5 grams of example #1, i.e., AMP3. Nitrogen flow was maintained throughout. To this was added 82.5 grams of C12–C14-α-Olefin Epoxide (70:30). The initial alkalinity of this mixture was 296 mg KOH/g. The temperature was raised to 150° C. with continued nitrogen atmosphere. Reaction was continued at 150° C. for the duration of 2 hours. The alkalinity remained constant indicating that there was no loss of amine equivalence. The reaction mass was a dark amber liquid. Upon cooling to 30° C. the yield was 250 grams.

EXAMPLE #50

(121-96)

Preparation of Quat P3LM (DES Quat of AMP3LM)

In a 500 ml four neck glass reaction flask was added 137.37 grams of AMP3LM from example #49 (reference 121.95). The inert atmosphere of nitrogen was maintained throughout. Temperature was raised to 55° C. at which time the addition of DES (diethyl sulfate) was started so that the exotherm came to approximately 85° C.–104° C. Total quantity of DES was 112.62 grams of which the first portion was 35.57 grams. The balance of DES was added in units of 23.71 grams at temperature of 100° C.–104° C. Each portion was reacted for 30 minutes before the next portion of DES was added. Alkalinity and pH were checked on the in-process sample. Alkalinity was none and pH 25% solution in water was 1.2. Reaction was cooled to 80° C. Added 35 grams of 1,3-butylene glycol and the mass was mixed for 1 hour at 80° C. The mixture was then cooled to 30° C. The yield of 280 gams was obtained as a semisolid paste. This is abbreviated as Quat P3LM.

EXAMPLE #51

(121-98)

Preparation of Aqueous Quat P3LM

In 1 500 ml glass reaction flask was added 75 grams of the product of example #50 (i.e. anhydrous Quat P3LM) and 225 grams of water. Mixture was subjected to mixing and pH adjustments with a 25% w/w sodium hydroxide solution. The pH was brought to 5.9. Mixture was brought to 80° C. under nitrogen. It was then subjected to a reduced pressure of 15"–20" Hg and held there for 1 hour. 30 grams of the distillate were collected. Added 30 grams of water to the reaction flask and equalized the pressure to 1 atmosphere. Cooled to 30° C. The yield of this mixture was 300 grams in the form of a fluid dispersion.

EXAMPLE #52

Comparative Substantivity Properties

Substantivity is defined as the ability of the quaternary (or cationic) substance to be attracted to an anionic surface such as hair and wool. Substantivity is taken as a conditioning efficacy parameter for hair care products. In the industry, the Rubine Dye Uptake Test is typically performed to screen for the property of substantivity.

A control fabric swatch of wool is treated in water without any treatment with a quaternary compound. The test articles, i.e., fabric swatches, are applied with a certain level of "activity" to the same weight fabric swatches as the control swatch. The treated fabric swatches are rinsed and then further treated in a solution of anionic acid dye such as Rubine Red Dye. The treatment with dye solution allows the fabric to attract the strong anionic dye solution with the help of a quaternary compound that has been applied to the swatch. The depth of color is stronger or weaker depending upon the substantivity (higher or lower) of the quaternary. The deeper the color, the greater the substantivity of the quaternary.

The Rubine Dye Uptake Test was performed using the following materials:

1. Wool (Worsted) Swatches:
   Size=3½ inches×5½ inches
   Weight=2.6 gm.
2. Dye Solution:
   0.50 gms. Dye (Direct Red #207, i.e., Lumicrease Bordeaux 3LR, Clariant, Inc., Charlottte, N.C.
   0.125 gms. Glacial Acetic Acid
   q.s. Water
   1000 mls.
3. Dye Solution for Test Swatch:
   150 mls. for each swatch
4. Test Sample Quaternary Solution:
   0.5% Active Quaternary in Water
   i.e., 1.0 gm. of Active Quaternary in 200 ml. Water Procedure The control swatch is treated in water without quaternary compound. Separate swatches for each quaternary substance are treated for 5 minutes with mild stirring in separate beakers. The swatches are then individually (separately) rinsed with water.

The control swatch and treated swatches are further treated (each one in a separate beaker) with dye solution for 5 minutes and rinsed in tap water at 40° C. The swatches are allowed to air dry.

The depth of the dye uptake is compared. The higher the color depth, the higher the substantivity of the quaternary.

The results of the test are set forth in Table II below, where a substantivity rating of 1 is the best, and a rating of 10 is poor.

TABLE II

Comparative Substantivity Properties

| TEST ARTICLES | % ACTIVE QUATERNARY | INCI NAME | RATINGS |
|---|---|---|---|
| No Conditioner (Control) | None | — | 10 |
| FINQUAT ® CT[1] | 0.50 | Quaternium 75 | 3 |
| FINQUAT ® CT-P[2] Product of Invention Example #6, 9, 20) | 0.50 | Quaternium 89 | 1 |
| Stearalkonium Chloride (Stearyl Trimethyl Ammonium Chloride) | 0.50 | Stearalkonium Chloride | 2 |
| Cetyl Trimethyl Ammonium Chloride | 0.50 | Cetrimonium Chloride | 2 |
| Dimethyldiallyl Ammonium Chloride[3] | 0.50 | Poly Quaternium 7 | 2 |
| Dimethyldiallyl Ammonium Chloride[3] | 1.78 | Poly Quaternium 7 | 2 |

[1]Finextex, Inc., Elmwood Park, NJ.
[2]Finextex, Inc., Elmwood Park, NJ.
[3]Calgon, Inc., Pittsburgh, PA.

As can be seen in Table II, FINQUAT® CT-P (the product of Examples #6, 9 and 20) shows superior substantivity in this group of quaternaries tested. This is indicative of high substantivity for its use as a conditioning agent for hair care products. Hair is similar to wool fibers. Accordingly, wool is used as a sample textile material, serving a dual purpose in testing quaternaries.

EXAMPLE #53

Comparative Conditioning Properties

Conditioning efficacy is judged by evaluating wet and dry comb characteristics and flyaway features of the hair tresses treated with the conditioners.

A comparative study was done using the quaternary of this invention (Product of Example #6, 9, 20) known commercially as FINQUAT® CT-P, as compared to other commercially marketed products.

A prototype formulation of Conditioner Base was made as shown below:

Water: Q.S. to 100 Parts
Hydroxyethyl Cellulose: 0.40 Parts
Propylene Glycol: 10.00 Parts
PEG-75 Lanolin: 0.25 Parts
Conditioner: Q.S. for 2.5% Actives Procedure Mix hydroxy ethyl cellulose in water. Dissolve completely at 50° C. Add propylene glycol and PEG-75 lanolin. Add conditioner and mix well. Cool to 25° C.

Conditioners used in the study:

1. Control (without any conditioner)
2. FINQUAT® CT (INCI Name: Quaternium 75)
3. FINQUAT® CT-P (INCI Name: Quaternium 89) (Product of Invention Example Nos. 6, 9, and 20, as in Table II)
4. Stearyl dimethyl ammonium chloride (INCI Name: Stearalkonium Chloride, the most widely used hair conditioner ingredient)
5. Cetyl trimethyl ammonium chloride (INCI Name: Cetrimonium Chloride)
6. Dimethyldiallyl ammonium chloride (INCI Name: Poly Quaternium 7)

The attached table gives the results of the test of comparaitive conditional properties, with a rating of 1 being the best, and a rating of 10 being poor.

TABLE III

Comparative Conditioning Properties

|  | WET COMB | DRY COMB | FLYAWAY (INCHES) |
|---|---|---|---|
| Control (No conditioner) | 8 | 5 | 3 |
| FINQUAT ® CT[1] (Quaternium-75) | 6 | 2 | 2.5 |
| FINQUAT ® CT-P[2] (Quaternium-89) (Product of Example #6, 9, 20) | 2 | 1 | 2 |
| Stearalkonium Chloride (Stearyl Trimethyl Ammonium Chloride) | 5 | 4 | 4.5 |
| Cetrimonium Chloride | 7 | 3 | 4.0 |
| Dimethyldiallyl Ammonium Chloride[3] (Polyquaternium 7) | 7 | 4 | 4.0 |

[1]Finextex, Inc., Elmwood Park, NJ.
[2]Finextex, Inc., Elmwood Park, NJ.
[3]Calgon, Inc., Pittsburgh, PA.

As can be seen in Table III, FINQUAT® CT-P (the product of Examples #6, 9 and 20) shows superior conditioning properties in this group of quaternaries tested. This is indicative of its benefits for use as a conditioning agent for hair care products.

Example #54

Toxicology Studies

Toxicology studies compared the new quaternary ammonium compound of the invention (hereinafter referred by its tradename FINQUAT® CT-P) to FINQUAT® CT, available from Finetex, Inc. of Elmwood Part, N.J. The studies indicate that the new quaternary ammonium compound of the invention, FINQUAT® CT-P, is milder than FINQUAT® CT, which itself is a mild quaternary.

Both products were tested at 3.0% active for dermal and ocular irritation by in-vitro Mat Tek Protocols (Skin model and Ocular Tissue model).

Construction of a Dose Response Curve: The extractant solution within each well was pipetted up and down several times to insure that each is well mixed. 200 microliters of each of the mixed extraction solutions was then pipetted into separate wells of a 96 well microtiter plate. A Dynatech MR 4000 Automatic Microplate Reader was used to determine the optical density of each extract at 570 nm. With the absorbance of a negative control defined as 100%, the percent absorbencies of the articles were determined (% viability=100×(OD [article]/OD [negative control]). The calculated percentages directly correlate with the cell metabolism in the Epiocular samples.

Using a semi-log scale, the percent viability (liner "y" axis) was plotted versus the dosing time (log "x" axis). By interpolation, the time at which the viability has dropped to 50% was determined.

Correlation of In Vitro and In Vivo Results: (Epi-Ocular) The following equation was used to estimate the rabbit Draize eye score: Log Draize=2.067−(0.979×Lot ET-50 (min)). Based on the literature (Kay, J. H. and Calandra, J. C., "Interpretation of Eye Irritation Tests," J. Soc. Cosmetic Chem., 13, 281–289 (1962), the ocular irritancy can be categorized into the following groups based on the Draize score:

| Draize Score | Irritancy Classification | Example | Epiocular ET-50 (min). |
|---|---|---|---|
| 0–15 | Non-irritating, Minimal | PEG-75 Lanolin, Tween 20 | >240–20.5 |
| 15.1–25 | Mild | 2% Sodium Dodecyl Sulfate | <20.5–9.67 |
| 25.1–50 | Moderate | 5% Triton X-100 | <9.67–3.48 |
| 50.1–110 | Severe, Extreme | 5% Benzalkonium Chloride | <3.48 |

Correlation of In vitro and In vivo results: (EpiDerm) The following groupings were used in assigning expected in vivo irritancy responses based upon the Et-50 results obtained using the EpiDerm:

| ET-50 (hrs) | Expected In vivo Irritancy | Example |
|---|---|---|
| <0.5 | Severe, probably corrosive | Conc. Nitric Acid |
| 0.5–4 | Moderate | 1% Sodium Dodecyl Sulfate |
| 4–12 | Moderate to mild | 1% Triton X-100 |
| 12–24 | Very mild | Baby Shampoo |
| 24 | Non-irritating | 10% Tween 20 |

The results are:

| Ocular Results/Classification | |
|---|---|
| FINQUAT ® CT = | Minimal Irritancy (as in Tween) |
| FINQUAT ® CT-P = | Non-Irritancy (as in Peg 75 Lanolin) |
| Positive Control = Triton X-100 0.3% | Mild Irritancy |

| Dermal Results/Classification | |
|---|---|
| FINQUAT ® CT = | Very mild range |
| FINQUAT ® CT-P = | Non-Irritating range |
| Positive Control = Triton X-100 0.3% | Moderate to mild range |

It will be understood that the embodiments described herein are merely exemplary and that a person skilled in the art may make many variations and modifications without departing from the spirit and scope of the invention. For example, the invention is not intended to be strictly limited to the named reactants and catalysts, recited pH ranges, reaction temperatures, reaction conversion, or other parameters. Rather, the invention as claimed extends to many possible variations not specifically detailed. All such variations and modifications are intended to be included in the scope of the invention as described herein.

We claim:

1. A quaternary ammonium compound represented by the following structure:

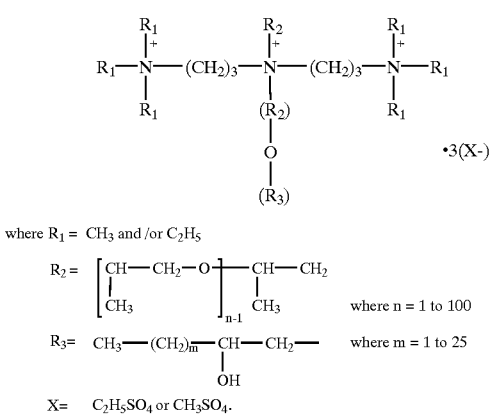

where $R_1 = CH_3$ and /or $C_2H_5$ $R_2 = \left[ CH(CH_3)-CH_2-O \right]_{n-1} CH(CH_3)-CH_2-$ where $n = 1$ to $100$ $R_3 = CH_3-(CH_2)_m-CH(OH)-CH_2-$ where $m = 1$ to $25$ $X = C_2H_5SO_4$ or $CH_3SO_4$.

2. A quaternary ammonium compound represented by the following structure:

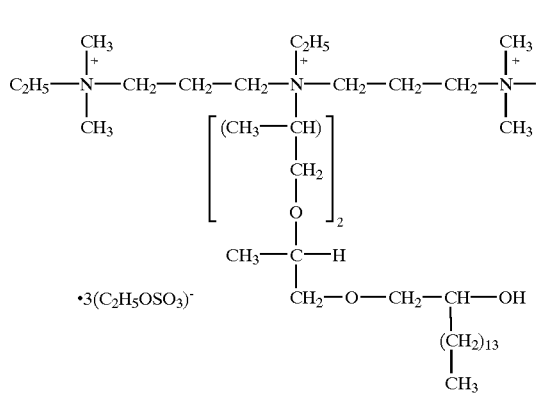

3. A quaternary ammonium compound represented by the following structure:

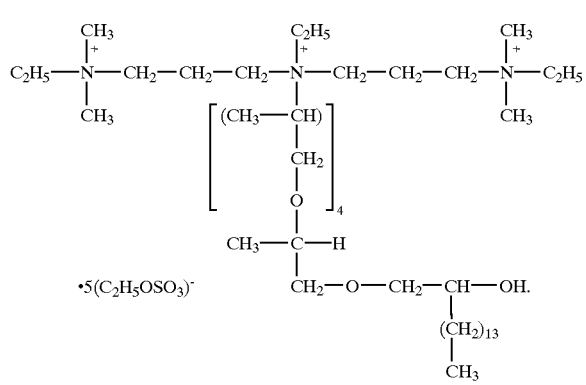

4. A quaternary ammonium compound represented by the following structure:

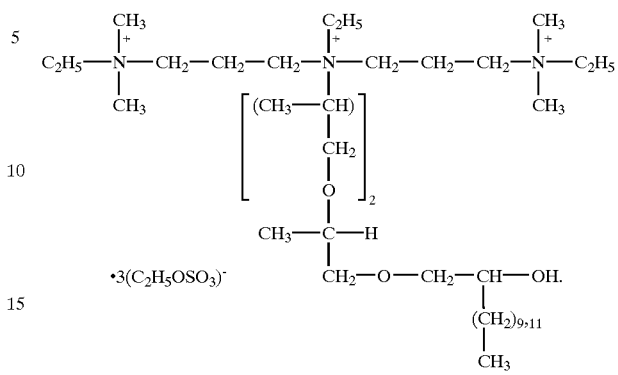

5. The quaternary ammonium compound of claim 1 formed by reacting diethyl sulfate and hydroxycetylalkylated condensate of propxylated or ethoxylated tetramethyliminobis propylamine represented by the following structure:

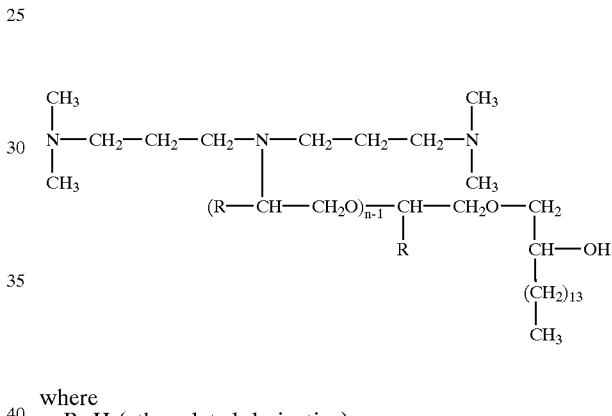

where
R=H (ethoxylated derivative);
R=$CH_3$ (propxylated derivative); and
n=1 to 100 moles of Ethylene Oxide and/or Propylene Oxide.

6. A process for preparing the quaternary ammonium compound of claim 1, comprising:
(a) reacting a substituted, dipropylene triamine with alkoxide to produce a polyoxypropylene adduct amine of alkoxide;
(b) reacting the adduct of step (a) with a 1,2 epoxyalkane having from 3 to 28 carbon atoms to produce a hydroxyalkoxy-polyalkoxylated tetramethyliminobis propylamine;
(c) quaternizing each mole of the hydroxyalkoxy-polyalkoxylated tetramethyliminobis propylamine of step (b) with a quaternizing agent to yield a quaternary ammonium compound having the following structure:

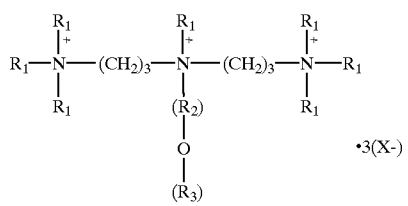

-continued where $R_1 = CH_3$ and/or $C_2H_5$

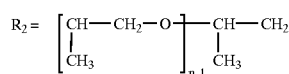 where n = 1 to 100

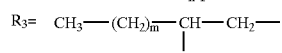 where m = 1 to 25

$X = C_2H_5SO_4$ or $CH_3SO_4$.

7. The process of claim 6 wherein the substituted, dipropylene triamine of step (a) comprises Tetramethyliminobis-Propylamine.

8. The process of claim 6 wherein said alkoxide of step (a) is selected from the group consisting of propylene oxide, ethylene oxide, and a mixture of ethylene oxide and propylene oxide.

9. The process of claim 6 wherein the 1,2 epoxyalkane of step (b) comprises $C_{16}$-α-olefin epoxide.

10. The process of claim 6 an wherein said quaternizing agent of step (c) is selected from the group consisting of diethyl sulfate, dimethyl sulfate, methyl chloride, methyl bromide and methyl iodide.

11. The process of claim 6 wherein after step (c), the step of diluting the quaternary ammonium compound produced in step (c) in water to obtain the desired concentration.

12. The process of claim 11, wherein the concentration is in the range of 25% to 75% solids-liquid solution or dispersion.

13. The process of claim 6 wherein 1 mole of a substituted, dipropylene triamine is reacted with 3 moles of propylene oxide.

14. The process of claim 6 wherein 1 mole of a substituted, dipropylene triamine is reacted with 5 moles of propylene oxide.

15. The process of claim 6 wherein said hydroxyalkoxy-polyalkoxylated tetramethylimnobis propylamine is hydroxycetoxy-polyoxypropylated tetramethyliminobis propylamine.

16. The process of claim 6 wherein said hydroxyalkoxy-polyalkoxylated tetramethyliminobis propylamine is hydroxy(lauryl/myristyl)oxy-polyoxypropylated tetramethyliminobis propylamine.

17. A fiber conditioning composition comprising a conditioning effective amount of at least one quaternary ammonium compound as defined in claim 1.

18. A cosmetic hair care formulation comprising at least one quaternary ammonium compound as defined in claim 1.

19. A softening, conditioning and antistatic composition for hair, fibers, and textiles, comprising:
(a) a carrier; and dispersed therein, (b) a softening, conditioning and antistatic effective amount of at least one of the quaternary ammonium compounds represented by the general formula of claim 1.

20. The composition of claim 16 further comprising one or more components selected from the group consisting of surfactants, neutralizers, stabilizers, coloring agents, fragrances, plasticizers, foam stabilizers, film forming polymers, preservatives, antistats, sequestrants, water, dyes, perfume, thickeners, preservatives, plant extracts, and customary additive and auxiliary substances.

21. The composition of claim 19 wherein said quaternary ammonium compound comprises at least from 0.5% to 10% by weight of said composition.

22. A method for softening and conditioning hair, fibers, or textiles comprising applying to said hair, fibers, or textiles for a sufficient time a softening and conditioning effective amount of at least one of the quaternary ammonium compounds represented by the general formula of claim 1.

* * * * *